United States Patent [19]
Zewert et al.

[11] Patent Number: 5,749,847
[45] Date of Patent: May 12, 1998

[54] DELIVERY OF NUCLEOTIDES INTO ORGANISMS BY ELECTROPORATION

[75] Inventors: Thomas E. Zewert, Boston; Uwe Pliquett, Cambridge; Robert S. Langer, Newton; James C. Weaver, Sudbury, all of Mass.

[73] Assignee: Massachusetts Institute of Technology, Cambridge, Mass.

[21] Appl. No.: 471,642

[22] Filed: Jun. 6, 1995

Related U.S. Application Data

[63] Continuation-in-part of Ser. No. 96,512, Jul. 23, 1993, Pat. No. 5,547,467, which is a continuation-in-part of Ser. No. 705,778, May 28, 1991, abandoned, which is a continuation-in-part of Ser. No. 331,263, Mar. 30, 1989, Pat. No. 5,019,034, which is a continuation-in-part of Ser. No. 146,343, Jan. 21, 1988, abandoned.

[51] Int. Cl.$^6$ .................................................. A61M 31/00
[52] U.S. Cl. .................................................. 604/49; 604/20
[58] Field of Search .................... 604/20–21, 890.1; 514/947; 435/173.6, 173.4

[56] References Cited

U.S. PATENT DOCUMENTS

| | | | |
|---|---|---|---|
| 578,611 | 3/1897 | Rively . | |
| 3,078,850 | 2/1963 | Schein et al. | 128/419 |
| 3,614,955 | 10/1971 | Mirowski et al. | 128/419 |
| 3,680,544 | 8/1972 | Shinnick et al. | 128/2 R |
| 4,411,648 | 10/1983 | Davis et al. | 604/21 |
| 4,784,737 | 11/1988 | Ray et al. | 204/180.1 |
| 4,955,378 | 9/1990 | Grasso | 128/421 |
| 4,979,948 | 12/1990 | Geddes et al. | 606/33 |
| 5,007,995 | 4/1991 | Takahashi et al. | 204/299 R |
| 5,019,034 | 5/1991 | Weaver et al. . | |
| 5,047,007 | 9/1991 | McNichols et al. | 604/20 |
| 5,098,843 | 3/1992 | Calvin . | |
| 5,137,817 | 8/1992 | Busta et al. | 435/173 |
| 5,141,742 | 8/1992 | Brown et al. . | |
| 5,286,717 | 2/1994 | Cohen et al. . | |
| 5,296,222 | 3/1994 | Petersen et al. . | |
| 5,383,848 | 1/1995 | Hillman et al. . | |
| 5,389,069 | 2/1995 | Weaver . | |
| 5,445,609 | 8/1995 | Lattin et al. . | |
| 5,462,520 | 10/1995 | Hofmann . | |

FOREIGN PATENT DOCUMENTS 9309789  5/1993  WIPO .

OTHER PUBLICATIONS

Mir et al., "Improvement of Anticancer Electrochemotherapy," *Proceedings of the American Association for Cancer Research*, 30:571, Abstract No. 2274 (1989).

Mir et al., "Pharmacological Applications of Electropermeabilization of Living Cells," Lab. de Biochimie–Enzymologie, Institut Gustave–Roussy 94805 Villejuif Cedex–France.

Mir et al., "Potentiation of Bleomycin by Local Electric Pulses: Experimental Anticancer Electrochemotherapy," *Proceedings of the American Association for Cancer Research*, 31:440, Abstract No. 2612 (1990).

Mir et al., "Electrochemotherapy Potentiation of Antitumour Effect of Bleomycin by Local Electric Pulses," *Eur. J. Cancer*, 27(1):68–72 (1991).

Okino et al., "Effects of a High–Voltage Electrical Impulse and an Anticancer Drug on In Vivo Growing Tumors," *Jpn. J. Cancer Res.*, 78(12):1319–1321 (1987).

(List continued on next page.)

*Primary Examiner*—Mark Bockelman
*Attorney, Agent, or Firm*—Hamilton, Brook, Smith & Reynolds, P.C.

[57] ABSTRACT

A method for delivering a nucleotide into an organism includes applying a composition which includes a nucleotide component to epidermis of the organism. The epidermis is electroporated, whereby at least a portion of the composition enters or passes across the epidermis, thereby delivering the nucleotide into the organism. An example of a suitable nucleotide which can be delivered by the method of the invention includes antisense oligodeoxynucleotides for treatment of melanomas.

49 Claims, 3 Drawing Sheets

OTHER PUBLICATIONS

Héroux et al., "Assessment of Trauma in Tissue by Electrical Impedance Measurements," *Electromagnetics in Biology and Medicine,* pp. 215–221 (1991).

Bhatt et al., "Rhabdomyolysis Due to Pulsed Electric Fields," *Plastic and Reconstructive Surgery,* 86(1):1–11 (1990).

Heller et al., "Transfer of Human Membrane Surface Components by Incorporating Human Cells into Intact Animal Tissue by Cell–Tissue Electrofusion In Vivo," *Biochimica et Biophysica Acta,* 1024:185–188 (1990).

Titomirov et al., "In Vivo Electroporation and Stable Transformation of Skin Cells of Newborn Mice by Plasmid DNA," *Biochimica et Biophysica Acta,* 1088:131–134 (1991).

Okino et al., "Intracellar Bleomycin Concentration and Histological Examination in Electrical Impulse Chemotherapy," *J. of Japan Soc. for Cancer Therapy,* 22(8):337 (1987).

Kanesada et al., "Anticancer Effects of Electrical Impulse Chemotherapy for the Primary and Metastatic Foci of Lewis Lung Carcinoma," *J. of Japan Soc. for Cancer Therapy,* 22(8):338 (1987).

Okino et al., "Electrical Impulse Chemotherapy for Rat Solid Tumors," *Japanese J. of Cancer Research,* Proceedings of the Japanese Cancer Association 46th Annual Meeting, Sep. 7–9, 1987, 46:420 (1987).

Tatsuka et al., "An Improved Method Of Electroporation for Introducing Biologically Active Foreign Genes into Cultured Mammalian Cells," *Experimental Cell Research,* 178:154–162 (1988).

Melvik et al., "Increase in Cis–Dichlorodiammineplatinum (II) Cytotoxicity upon Reversible Electropermeabilization of the Plasma Membrane in Cultured Human NHIK 3025 Cells," *Eur. J. Cancer Clin. Oncol.,* 22(12):1523–1530 (1986).

Kubota et al, "Toxicity and Metabolism of Ara–CTP Injected ino Cells by Elecroporation," *Proc. Amer. Assoc. Cancer Res.,* 31:397, Abstract 2356, (1990).

Duvanel et al., "New Technique to Perform Local Anesthesia: Pulsed Iontophoresis," *Dermatolog,* 177(1):30 (1988).

Tovar et al, "Electroporation and Recovery of Cardiac Cell Membrane with Rectangular Voltage Pulses," *Am. J. Physiol.,* 263:H1128–H1136 (1992).

Grasso et al., "Electrofusion of Individual Animal Cells Directly to Intact Corneal Epithelial Tissue," *Biochimica et Biophysica Acta,* 980:9–14 (1989).

Orlowski, et al., "Transient Electropermeabilization of Cells in Culture," *Pharmacology,* 37(24):4727–4733 (1988).

Mir et al., "L'électrochimiothérapie, un Noveau Traitement Antitumoral: Premier Essai Clinique," *C.R. Acad. Sic. Paris, 313 Serie III:*613–618 (1991).

Heller et al., "Development of Cell–Tissue Electrofusion for Biological Applications," *Guide to Electroporation and Electrofusion,* 393–410 (1992).

Prausnitz, et al., "Transtissue Molecular Transport Due to Electroporation of Skin, " *Electriciy and magnetism in Biology and Medicine,* 122–124 (1993).

Mir et al., "Electrochemotherapy: A New Antitumor Treatment Using Electric Pulses," *Electricity and Magnetism in Biology and Medicine,* 119–121 (1993).

Okino et al, "The Effects of a Single High Voltage Electrical Stimulation with an Anticancer Drug in vivo Growing Malignant Tumors," *Jpn. J. of Surgery,* 20(2):197–204 (1990).

R. Heller, "Incorporation of Individual Cells into Intact Tissue by Electrofusion," *Electricity and Magnetism in Biology and Medicine,* 115–117 (1993).

Weaver, James C., "Electroporation: A General Phenomenon for Manipulating Cells and Tissues," *Journal of Cellular Biochemistry,* 51(4):426–435 (1993).

Prausnitz et al., "Electroporation of Mammalian Skin: A Mechanism to Enhance Transdermal Drug Delivery," *Proc. Nat'l Acad. Sci.,* 90:10504–10508 (1993).

Pransnitz et al., "Methods for In Vivo Tissue Electroporation Using Surface Electrodes," *Drug Delivery,* 1(2):125–131 (1993).

Hijiya et al., "Biologic and Therapeutic Significance of MYB Expression in Human Melanoma," *Proc. Nat'l Acad. Sci.,* 91:4499–4503 (1994).

Bergan et al., "Electroporation Enhances C–Myc Antisense Oligodeoxynucleotide Efficacy," *Nucleic Acids Research,* 21(15):3567–3573 (1993).

Zewert et al., "Transdermal Transport of DNA Antisense Oligonucleotides by Electroporation," *Biochemical and Biophysical Research Communications,* 212(2):286–292 (1995).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:1:

AACGTTGAGG GGCAT                  15

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:2:

TATGCTGTGC CGGGGTCTTC GGGC        24

DELIVERY OF NUCLEOTIDES INTO ORGANISMS BY ELECTROPORATION

RELATED APPLICATIONS

This is a continuation-in-part application of U.S. Ser. No. 08/096,512, filed Jul. 23, 1993, now U.S. Pat. No. 5,547,467 which is a continuation-in-part of U.S. Ser. No. 07/705,778, filed May 28, 1991, now abandoned, which is a continuation-in-part of U.S. Ser. No. 07/331,263, filed Mar. 30, 1989, now U.S. Pat. No. 5,019,034, which is a continuation-in-part of U.S. Ser. No. 07/146,343, filed Jan. 21, 1988, now abandoned, the teachings of all of which are incorporated by reference in their entirety.

GOVERNMENT FUNDING

The subject matter of this invention was partially supported by a grant, ARH4921, from the Government, which has certain rights in the invention.

BACKGROUND OF THE INVENTION

Many drugs and chemical agents are known to be effective in treatment of diseases. However, such agents also often have deleterious side effects when introduced into the organism in sufficient dosage to treat the targeted tissue.

One attempt to selectively treat diseased tissue is development of chemical agents which selectively affect only the diseased tissue. However, such chemical agents typically are only partially selective for the diseased tissue and often have a deleterious effect on healthy cells. Another attempt to selectively treat diseased tissue is to inject the chemical agent directly into the diseased tissue mass. However, the effect of chemical agents on diseased tissue is often dependent upon delivery of the chemical agent across cell membranes of the cells in the tissue mass as opposed to simply injecting the chemical agent into the tissue. Further, chemical agents which are injected into diseased tissue typically enter the bloodstream and are transported away from the targeted tissue mass before they have a significant therapeutic effect on the tissue mass into which they were injected.

In other specific applications of drugs, such as gene therapy, nucleotides are delivered to alter the behavior of cells. For example, antisense oligonucleotide therapy is based on the premise that transcription of a gene can be blocked when a cell is exposed to an antisense oligonucleotide corresponding to that gene. This gene can code, and thereby lead to the production of a protein which causes cancer (an oncogene) or a protein necessary for viral replication. Antisense oligonucleotide therapy for several forms of cancer (e.g., lymphomas and melanomas) and viruses (e.g., human t-cell leukemia virus (HTLV-I) and human immunodeficiency virus (HIV)) have been successfully performed in vitro and in mice.

However, there are many problems that are often associated with treatment of cells by conventional methods, such as intravenous injection. For example, the cells of melanoma tumors are typically difficult to target by injection techniques because they are in the form of relatively thin tissue. Further, injections can traumatize tissue, thereby possibly spreading potentially malignant growths. In addition, some therapeutic nucleotide compositions, such as those that include antisense oligonucleotides, are very expensive and, consequently, require very localized application. Also, use of some types of intravenous injection, such as intravenous infusion pumps, can be difficult to control and can promote infection. This complication is especially significant for patients afflicted with immunocompromising illnesses (e.g., leukemias and HIV infection).

Therefore, a need exists for a new method for delivering nucleotides into organisms.

SUMMARY OF THE INVENTION

The present invention relates to a new method for delivering a nucleotide into an organism.

The method includes applying a composition having a nucleotide component to epidermis of the organism. The epidermis is electroporated, whereby at least a portion of the composition enters or passes across the epidermis, thereby delivering the nucleotide into the organism.

The method of the invention is advantageous in several respects. First, the method enables topical treatment of skin lesions having a genetic component, such as melanoma tumors. This treatment is not invasive and delivery of nucleotides can be localized to the site of the lesion. Further, the amount of nucleotide necessary to treat a particular lesion is significantly reduced by localized application of the nucleotide, thereby substantially diminishing the cost of treatment. In addition, mechanical trauma, such as that caused by subcutaneous injections, is avoided by electroporation. Further, risk associated with disrupting cancer cells, such that they are moved to another location, thereby spreading the cancer, is lessened. With regard to systemic illnesses, delivery of nucleotides, such as antisense oligonucleotides, by the method of the invention can be controlled to ensure shut-off of the targeted gene over an extended period of time. Also, the likelihood of infection associated with delivery by intravenous injection is avoided by electroporation.

DETAILED DESCRIPTION OF THE INVENTION

Figure 1:
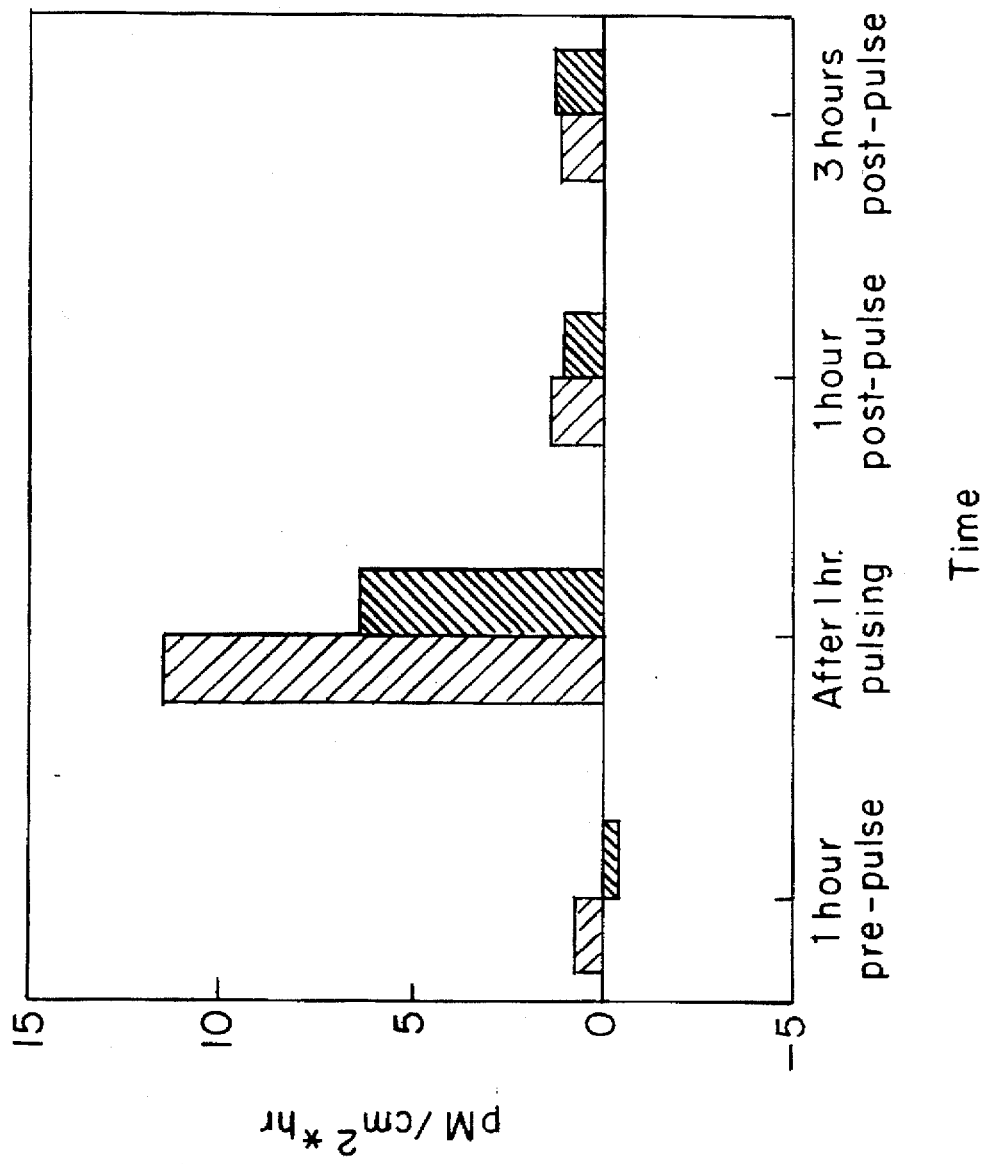
FIG. 1 shows a bar graph of fluorescein-labelled oligodeoxynucleotide transport through skin in vitro before, during, and after electroporation.

The features and other details of the method of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Generally, electroporation is a method of increasing the permeability of tissue and cell membranes. The increased permeability allows transport, or migration, of chemical agents through the tissue or across cell membranes into cells. For example, electroporation can include applying a voltage across tissue in vitro to cause the permeability of the tissue and cell membranes of cells in the tissue to increase. If the tissue is in the presence of a suitable chemical agent, the chemical agent can then migrate across the tissue or into cells of the tissue. Electroporation has also been used to deliver drugs to tissue, in vivo, by applying electrodes to the surface of an organism and applying a voltage between the electrodes which exposes the tissue to an electric field. The tissue thereby becomes electroporated and allows delivery of a chemical agent, such as a drug, which has been applied either topically to the organism or injected into the blood stream of the organism, across the electroporated tissue and into cells of the electroporated tissue.

"Electroporation," as that term is used herein, means increased permeability, of a cell membrane and/or at least a portion of cells of a targeted tissue, to a chemical agent, wherein the increased permeability is caused by application of voltage across the cell or at least a portion of the tissue. The chemical agent can thereby migrate into or across the electroporated tissue, and/or across the cell membrane and into the cell. Electroporation can include, for example, injuring at least a portion of the cells of targeted tissue to thereby cause the permeability of the tissue to significantly increase.

Examples of suitable apparatus and operation of the apparatus are disclosed in U.S. Ser. No. 07/705,778, filed May 28, 1991 and in U.S. Pat. No. 5,091,034, issued May 28, 1991, the teachings of which are incorporated by reference in their entirety. For example, electric pulses generated by suitable apparatus to cause electroporation by the method of the invention typically are exponential pulses having a time constant in the range of between about 0.1 and about three milliseconds, and an amplitude in the range of between about one hundred and about one thousand volts. However, the pulse configuration can also be square, bipolar, etc. Generally, the number of pulses sufficient to cause electroporation is in the range of between about one and about ten, wherein the interval between pulses is in the range of between about 0.01 second and one minute. Usually, the largest increase in permeability caused by electroporation occurs as a consequence of applying the first pulse.

The method of the invention includes delivering a nucleotide into an organism. In particular, the method includes applying a composition which includes a nucleotide component to epidermis of the organism and then electroporating the epidermis, whereby at least a portion of the composition enters or passes across the epidermis, thereby delivering the nucleotide into the organism.

Examples of suitable nucleotides include polynucleotides, oligonucleotides, deoxyribonucleotides and oligodeoxyribonucleotides. Other specific examples of suitable nucleotides include deoxynucleotides, such as oligodeoxynucleotides. Examples of suitable oligodeoxynucleotides include antisense oligodeoxynucleotides, such as an antisense oligodeoxynucleotide which corresponds to at least a portion of a codon sequence in a c-myc gene. For example, the antisense oligodeoxynucleotide can be a 15-mer having a nucleotide sequence of 5'-AACGTTGAGGGGCAT-3' (SEQ. ID NO: 1). The c-myc antisense oligodeoxynucleotide can correspond to codons 1–5 of the c-myc gene.

Alternatively, the antisense oligodeoxynucleotide can correspond to at least a portion of a codon sequence in a c-myb gene. For example, the antisense oligodeoxynucleotide can be a 24-mer having a nucleotide sequence of 5'-TATGCTGTGCCGGGGTCTTCGGGC-3' (SEQ. ID NO: 2). The c-myb antisense oligodeoxynucleotide can correspond to codons 2–9 of the c-myc gene.

Examples of other suitable components of the composition applied to the epidermis of the organism include, for example, a reducing agent, such as a charged reducing agent, that disrupts crosslinked keratin within keratinocytes of the epidermis.

Optionally, the epidermis can be pretreated by application of a suitable polyanion. Examples of suitable polyanions to inhibit non-specific deoxyribonucleic acid (DNA) binding and, thus, diminish the amount of DNA which, following electroporation, might be trapped in the epidermis. Examples of suitable polyanions include bovine serum albumin and ficol.

In another option, the epidermis can be treated by application of a proteinase, such as keratinase, papain, or reducing agents or compounds, to overcome hindrance of DNA transport during electroporation that might be caused by the dense keratin matrix of the epidermis.

A sufficient voltage is applied to the portion of the epidermis to which the composition was applied to cause a fraction of the area of that portion of the epidermis to become electroporated. Typically, the epidermis is electroporated by achieving a transdermal voltage of at least about 80 volts. In one embodiment, the transdermal voltage is applied as a series of pulses. In a specific embodiment, the pulsed-applied transdermal voltage has an average duration in a range of between about 1.1 milliseconds and about 2.2 milliseconds per pulse.

The electroporated portion of the epidermis can include the stratum corneum. As a consequence of electroporation, the applied composition at the epidermis enters the epidermis. In one embodiment, the composition can pass across the epidermis from a first side of the epidermis to a second, basal side of the epidermis. Optionally, electroporation of the skin can be conducted in conjunction with an additional electrical protocol, such as iontophoresis. The additional application of an electrical field can be conducted prior to, during, or after electroporation of the epidermis.

In another embodiment, the composition applied to the epidermis can be a vaccine, such as a vaccine that includes a plasmid deoxyribonucleic acid component. Alternatively, the composition can include a deoxyribonucleotide analog, such as azidodeoxythymidine, dideoxyinosine, dideoxycytosine, gancyclovir, acyclovir, vidarabine, ribavirin, etc.

In other embodiments, the composition can include a label, such as a radioactive label. Alternatively, the composition can include a photoactive modification, such as Psoralin C2.

In still another embodiment, the composition can include a phosphoramidate linkage, such as butylamidate, piperazidate, and morpholidate. Alternatively, the composition can include a phosphothiolate linkage or ribonucleic acid. These linkages decrease the susceptibility of the oligonucleotides and polynucleotides to degradation.

Optionally, the electrical resistance or impedance of the epidermis can be measured during electroporation to thereby monitor the amount of electroporation that has occurred.

In another embodiment, a composition which includes a nucleotide can be applied to a tissue within an organism. The tissue is electroporated, whereby at least a portion of the composition enters or passes across the tissue, thereby delivering the nucleotide into the tissue. Suitable apparatus for conducting this embodiment of the method of the invention are disclosed in U.S. Pat. No. 5,389,069, the teachings of which are incorporated herein by reference in their entirety.

The invention will now be further and specifically described by the following examples. All parts and percentages are by weight unless otherwise specified.

EXEMPLIFICATION

Materials and Methods

Fluorescein Labeled Oligonucleotide (ODN) Synthesis and Purification 1 mMole of each ODN was synthesized fully phosphorothioated on an Applied Byosystems 380B DNA Synthesizer. (G. Zon, W. J. Steck, in "Oligonucleotides and Analogues: A Practical Approach," F. Eckstein, Eds. (Oxford Univ. Press, Oxford, 1991), pp. 87–108.) The use of phosphorothioate linkages has been shown to greatly decrease nuclease digestion. A fluorescein CPG support (Glen Research, Sterling, Va.) was used so that the fluorescein derivative was directly incorporated into the backbone of the ODNs at the 3' end from the start of the synthesis. ODNs were ethanol precipitated, washed in 70% ethanol, detritylated and further purified using NENSORB PREP cartridges (E. I. duPont de Nemours & Co., NEN Products, Boston, Mass.). Purity (i.e., no smaller ODNs or free fluorescein) was confirmed by denaturing polyacrylamide electrophoresis prior to and after electroporation. The sequence for the antisense 15-mer of c-myc and the 24-mer of c-myb were 5'-AACGTTGAGGGGCAT-3' (SEQ. ID NO. 1) and 5'-TATGCTGTGCCGGGGTCTTCGGGC-3' (SEQ. ID NO. 2), respectively. The c-myc antisense ODN was 4.8 kDa and corresponded to codons 1–5 of the c-myc gene; the c-myb antisense ODN was 7.0kDa and corresponded to codons 2–9 of the c-myb gene.

Skin Preparation

Heat-stripped stratum corneum was used in all experiments (area exposed to the electrical field 0.7 cm$^2$). (M. R. Prausnitz, et al., *Proceed. Intern. Symp. Control. Rel. Bioact. Mater.*, 20, 95–96 (1993)). The skin was obtained from either the abdomen, arm, or back of adult human cadavers. Prior to heat-stripping the skin was stored at $-70°$ C. for one to six months. After heat-stripping, the skin was stored at $4°$ C. in a 95% humidity environment.

Pulse Application and Electrical Measurements

High-voltage pulses were delivered using an exponential pulser (Electroporation System 600, BTX Industries, San Diego, Calif.) modified for automated control. The pulse time constants $t_{pulse}$ was varied from 1.0 to 2.2 ms (using 50 Q to 720 W internal shunt resistance) with 0.1 ms variation during an experiment. A side-by-side permeation chamber was used. Two pairs of Ag/AgCl electrodes constructed from 16-gauge silver wire were used for both the application and sensing of voltage. The donor compartment was at the negative and the receptor compartment at the positive side of the pulser. This forward direction polarity provided an electrophoretic driving force through the skin for the negatively charged fluorescent molecules. A voltage divider effect involving the bathing solution, electrodes, and skin resulted in the transdermal voltage being much less than the pulsing voltage. Voltage traces were acquired and stored on a Hewlett-Packard 54601 digital oscilloscope.

Image Acquisition

A biocular fluorescence microscope (Olympus BH-2) was used, together with an Olympus OM2 camera. Shutter times were between 0.25 and 3 seconds.

Fluorescent Molecule Transport Across the Stratum Corneum

The concentration of ODN in the donor compartment was 25 mm. The fluorescence of the receptor compartment solution was measured using a spectrofluorimeter (Fluorolog 2, Model F112AI, SPEX Industries, Edison, N.J.). To visualize sites of local transport, a 2% agarose solution in phosphate-buffered saline at $40°$ C. was added to the receptor compartment after one hour of pulsing, and allowed to gel for five minutes. A flow-through water jacket ($23°±30°$ C.) in the side-by-side apparatus was connected during these procedures. (M. R. Prausnitz, V. G. Bose, R. Langer, J. C. Weaver, *Proc. Natl. Acad. Sci. USA*, 90, 10504–10508 (1993)). Pulsing at approximately 80 V transdermal was carried out for three minutes, and then the agarose was viewed under a long-wave UV lamp for fluorescence visualization.

Imaging of Small Ion Transport Regions

Figure 4:
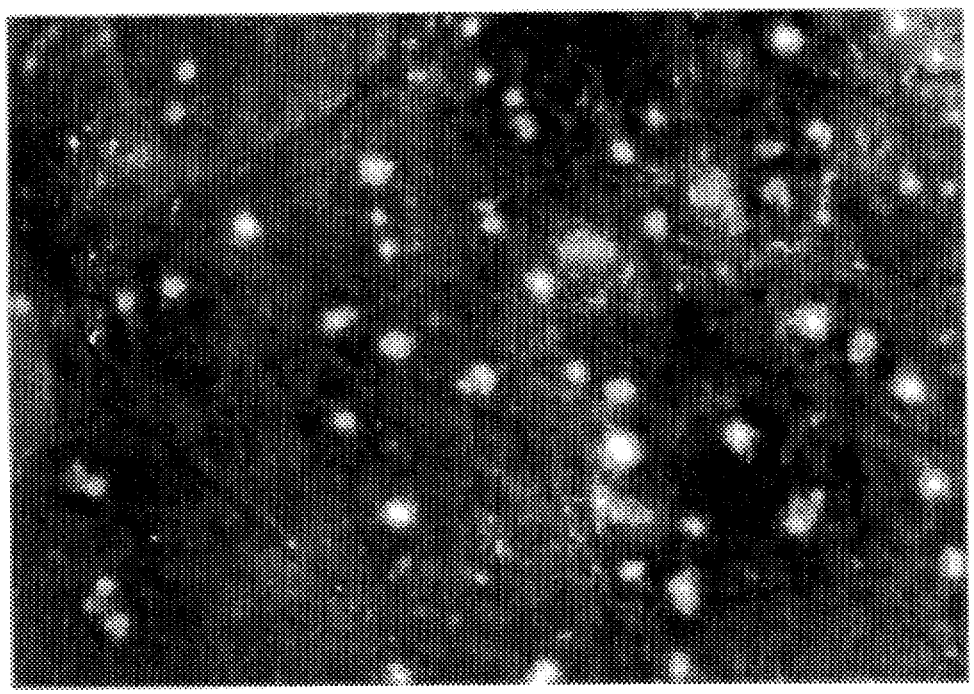
FIG. 4 is a photograph showing distribution of fluorescein-labelled oligodeoxynucleotide in skin in vitro.

To examine regions which retained transport ability up to several hours after pulsing, we removed the skin from the side-by-side apparatus and then placed it on a polished silver surface with the stratum corneum side touching the surface. Iontophoresis (1 mA for 30 seconds) was performed, and sites of ion deposition onto the silver were noted, as can be seen in FIG. 4.

Results

FIG. 1 is a bar graph of fluorescein ODN transport through the skin. Total molecular flux of fluorescein-labeled c-myc and c-myb ODNs for one hour prior to pulsing, during one hour of exponential ($t_{pulse}$=1.1 ms) pulsing at 80 V ($U_{skin}$) every five seconds, for one hour after pulsing, and for three hours further after pulsing. The flux standard deviation during pulsing is 3.5 for c-myc and 2.1 for c-myb. The errors in the other flux measurements were greater than 1.5 pM/cm$^2$ * hr; therefore, the measured value corresponding to flux before and after pulsing was less than the statistical error inherent in the measurement.

FIG. 1 shows that there was no significant flux of either of the fluorescein ODNs either before or after pulsing; whereas, significant transport occurs during pulsing. Statistically significant flux values for passive flux after pulsing were not obtained after even the highest voltage.

Figure 2:
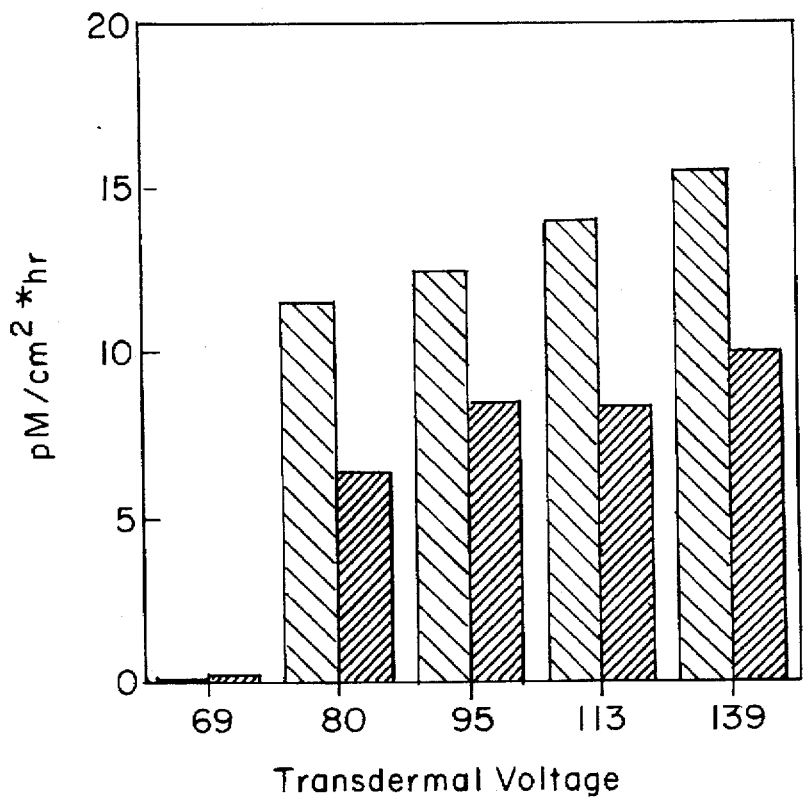
FIG. 2 shows a bar graph of fluorescein-labelled oligodeoxynucleotide transport through skin in vitro as a function of transdermal voltage.

FIG. 2 is a bar graph of fluorescein ODN transport through skin as a function of transdermal voltage. The conditions are the same as those set forth for the example represented by FIG. 1. FIG. 2 shows a sharp increase in transport of both fluorescein ODNs in raising the transdermal pulse voltage from 69 V to 80 V. The transport at 69 V is less than the error associated with the measurement, but increasing the voltage from 80 V to 139 V increases transport about one standard of deviation for fluorescein c-myc. The amount of flux appeared to plateau above 80 V.

Figure 3:
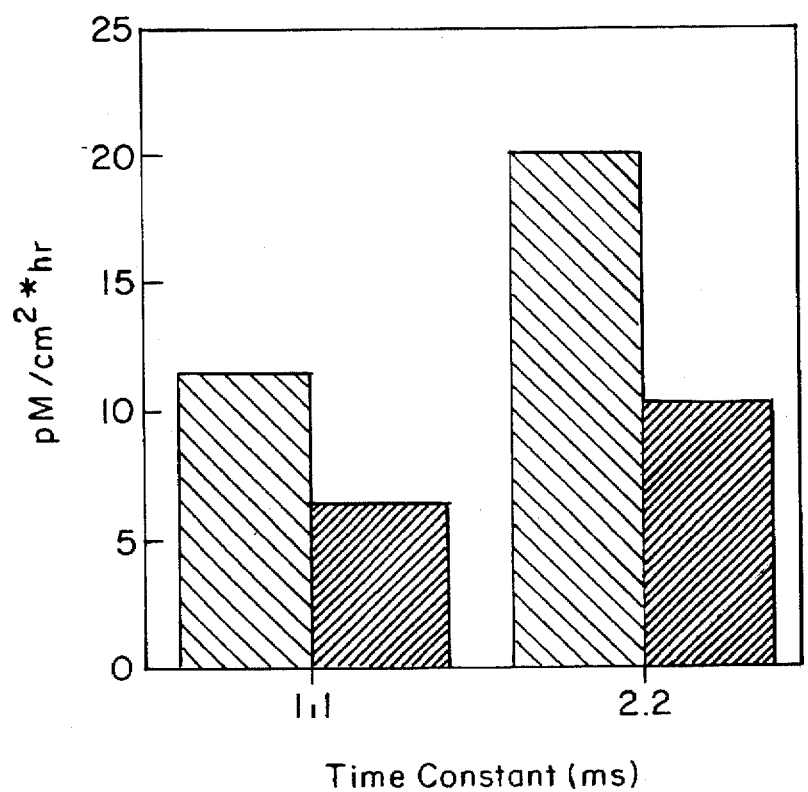
FIG. 3 is a bar graph of fluorescein-labelled oligodeoxynucleotide transport through skin in vitro, as a function the duration of a pulse-time constant.

FIG. 3 is a bar graph of fluorescein ODN transport through skin as a function of pulse time constant. The conditions are the same as those set forth for the example represented by FIG. 1. FIG. 3 shows that transport of both c-myc and c-myb fluorescein ODNs increases with increasing exponential pulse time constant. Under almost all conditions the flux of the c-myc ODN is greater than that of the c-myb ODN, although the difference is typically on the order of one standard of deviation.

FIG. 4 is an image based on fluorescein ODN in the skin and ion transport through the skin. After pulsing at 92 V ($U_{skin}$), the skin was placed between an agarose gel disk containing PBS and a polished silver electrode (stratum corneum touching this electrode). Iontophoresis was then carried out by maintaining a constant current (1 mA) through the skin for 30 seconds with the polished silver electrode serving as the anode and the agarose disk attached to a cathode. Anions (mainly, chloride) deposited onto the anode after having traversed the skin creating the dark areas. The images are of the skin and underlying silver electrode after the agarose disk had been removed. Areas of localized fluorescein ODN staining were bright. Illumination with white light and blue light (480 nm cutoff). Comparing the bright and dark it was seen that the areas of fluorescent molecule and current flux roughly coincided, with the latter having been more diffuse.

As shown in FIG. 4, fluorescence microscopy revealed the fluorescein ODNs were localized to areas 26±8 mm in diameter in the skin. Further, fluorescent ODNs were observed to penetrate all of the keratinocyte layers of the stratum corneum, and no structural damage was observed at 400x within these areas. Fluorescent ODNs were always located in the area of the heat-stripped skin corresponding to the dermal papillae (troughs of the epidermis) and no localized regions of staining appears in the Rete pegs (crests of the epidermis). 135±24 localized centers of staining per $cm^2$ skin were observed after pulsing at 80 V with a time constant of 1.1 ms for one hour every 5 seconds. Significantly, there was little or no fluorescence in the skin appendages (hair follicles and sweat ducts).

A relationship between localized skin fluorescence and actual transport was established by retaining the fluorescent molecules crossing the stratum corneum within a 2% agarose gel in the receptor compartment of the side-by-side apparatus. The areas of fluorescence in the gel were much broader than those in the skin, presumably due to lateral diffusion within the gel. A fluorescent region in the gel always corresponded to a fluorescent region in the skin stained with fluorescent DNA corresponded to a fluorescent area in the gel. No staining of the agarose occurred at areas corresponding to sweat ducts and hair follicles, indicating that relatively few molecules had been transported through these structures.

The existence of ionic transport pathways which persist after pulsing was observed, as also shown in FIG. 4. Generally the areas with fluorescent molecule and current flux coincided, with the latter being larger.

Discussion

Fluorescein-labeled ODNs were transported through skin in vitro during high-voltage pulsing. Transport increased markedly for pulsing with the transdermal voltage more than about 70 V, but quickly plateaued, an effect which had also been observed for calcein uptake by red blood cell ghosts and yeasts. (M. R. Prausnitz, et al., *Biophys. J.*, 65, 414–422 (1993)) (E. A. Gift, J. C. Weaver, *Biochim. Biophys. Acta*, 1234:52–62 (1995). In contrast, transport increased with increasing $t_{pulse}$ from 1.1 to 2.2 ms. This result and the observation that passive flux was negligible suggested that electrophoresis during the electrical pulses was important.

The observation of fluorescence in all layers of the stratum corneum by stereomicroscopy and the retention of fluorescence in the agarose gel were direct evidence for localized transport regions (LTRs) across the skin. Moreover, these results were in accord with what has been seen for the transport of the smaller, negatively-charged molecules calcein and sulforhodaine across skin.

Transport during high-voltage pulsing occurred primarily in LTRs which did not correspond to appendages. Also, in the experiments with AgCl deposition during post-pulse iontophoresis, the deposition corresponding to the localized ODN fluorescence in the skin was, in general, greater (i.e., areas were darker) than the deposition behind the appendages. Similar results were seen for calcein and sulforhodamine for related pulsing protocols.

The fractional area of all the LTRs for ODN transport was $8\times10^{-4}$ (after 720 pulses at 135 V); this value was much less than that observed for calcein $8\times10^{-2}$ (after only 40 pulses ranging from 80 V to 158 V). Both of these values were significantly more than the fractional area $F_w \approx 5\times10^{-7}$ that was estimated to actually participate as transporting aqueous pathways. Lateral transport of the fluorescent molecules could explain the difference between these observed and theoretical values. Moreover, the ODNs may have spread less laterally due to their relatively large size. Further, only approximately one in twenty DNA-stained regions actually transported; therefore, the net $F_w$ is approximately $2\times10^{-5}$. Over 100 $ng/cm^2$-hr of DNA were transported through the human epidermis.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method for delivering a nucleotide component of a composition into an organism, comprising:

a) applying the compositions which includes the nucleotide components to stratum corneum of the organism, whereby said nucleotide component directly contacts said stratum corneum; and thereafter b) electroporating the stratum corneum, whereby at least a portion of the composition enters or passes across the stratum corneum, thereby delivering the nucleotide component into the organism.

2. The method of claim 1 wherein the nucleotide is a polynucleotide.

3. The method of claim 1 wherein the nucleotide is an oligonucleotide.

4. The method of claim 1 wherein the nucleotide is a deoxyribonucleotide.

5. The method of claim 4 wherein the deoxynucleotide is an oligodeoxyribonucleotide.

6. The method of claim 1 wherein the nucleotide is a deoxynucleotide.

7. The method of claim 6 wherein the deoxynucleotide is an oligodeoxynucleotide.

8. The method of claim 7 wherein the oligodeoxynucleotide is an antisense oligodeoxynucleotide.

9. The method of claim 8 wherein the antisense oligodeoxynucleotide corresponds to at least a portion of a codon sequence in a c-myc gene.

10. The method of claim 9 wherein the antisense oligodeoxynucleotide is a 15-mer having a nucleotide sequence of 5'-AACGTTGAGGGGCAT-3' (SEQ. ID NO. 1).

11. The method of claim 10 wherein the c-myc antisense oligodeoxynucleotide corresponds to codons 1-5 of the c-myc gene.

12. The method of claim 8 wherein the antisense oligodeoxynucleotide corresponds to at least a portion of a codon sequence in a c-myb gene.

13. The method of claim 12 wherein the antisense oligodeoxynucleotide is a 24-mer having a nucleotide sequence of 5'-TATGCTGTGCCGGGGTCTTCGGGC-3' (SEQ. ID NO. 2).

14. The method of claim 13 wherein the c-myb antisense oligodeoxynucleotide corresponds to codons 2-9 of the c-myc gene.

15. The method of claim 1 wherein the epidermis is electroporated by applying a transdermal voltage of at least about 80 volts.

16. The method of claim 15 wherein the transdermal voltage is achieved by applying a series of pulses.

17. The method of claim 16 wherein the pulsed applied transdermal voltage has an average duration in a range of between about 0.5 milliseconds and about 50 milliseconds per pulse.

18. The method of claim 1 wherein at least a portion of the composition enters the stratum corneum.

19. The method of claim 1 wherein the composition passes across the stratum corneum from a first side of said epidermis to a second side of said epidermis.

20. The method of claim 1 wherein said composition includes a vaccine.

21. The method of claim 20 wherein said vaccine includes a plasmid deoxyribonucleic acid component.

22. The method of claim 1 further including the step of applying a polyanion to the stratum corneum prior to electroporating said stratum corneum, thereby inhibiting non-specific DNA binding.

23. The method of claim 22 wherein said polyanion includes an albumin.

24. The method of claim 23 wherein said albumin includes bovine serum albumin.

25. The method of claim 22 wherein said polyanion includes ficol.

26. The method of claim 1 wherein the composition includes a deoxyribonucleotide analog.

27. The method of claim 26 wherein said deoxyribonucleotide includes azidodeoxythymidine.

28. The method of claim 26 wherein said deoxyribonucleotide includes dideoxyinosine.

29. The method of claim 26 wherein said deoxyribonucleotide includes dideoxycytosine.

30. The method of claim 26 wherein said deoxyribonucleotide includes gancyclovir.

31. The method of claim 26 wherein said deoxyribonucleotide includes acyclovir vidarabine.

32. The method of claim 26 wherein said deoxyribonucleotide includes acyclovir.

33. The method of claim 26 wherein said deoxyribonucleotide includes ribavirin.

34. The method of claim 1 wherein the composition includes a label attached to said nucleotide component.

35. The method of claim 34 wherein said label is a radioactive label.

36. The method of claim 1 wherein the composition includes a Psoralin C2.

37. The method of claim 1 wherein the composition includes a phosphoramidate linkage.

38. The method of claim 37 wherein said phosphoramidate linkage includes butylamidate.

39. The method of claim 37 wherein said phosphoramidate linkage includes piperazidate.

40. The method of claim 37 wherein said phosphoramidate linkage includes morpholidate.

41. The method of claim 1 wherein the composition includes a phosphothioate linkage.

42. The method of claim 1 wherein the composition includes ribonucleic acid.

43. The method of claim 1 further including the step of applying a proteinase to said stratus corneum prior to electroporating said epidermis.

44. The method of claim 43 wherein said proteinase includes keratinase.

45. The method of claim 43 wherein said proteinase includes papain.

46. The method of claim 1 wherein the applied composition further includes a reducing compound that causes disruption of crosslinked keratin within keratinocytes of said epidermis.

47. The method of claim 46 wherein the reducing compound of said applied composition is a charged reducing compound.

48. The method of claim 1, further including the step of measuring electrical resistance across the stratus corneum during electroporation, whereby electroporation of said epidermis can be monitored.

49. The method of claim 1 further including the step of measuring electrical impedance across the stratus corneum during electroporation, whereby electroporation of said epidermis can be monitored.

* * * * *

UNITED STATES PATENT AND TRADEMARK OFFICE
CERTIFICATE OF CORRECTION

PATENT NO. : 5,749,847  
DATED : May 12, 1998  
INVENTOR(S) : Thomas E. Zewert, Uwe Pliquett, Robert S. Langer and James C. Weaver Page 1 of 2

It is certified that error appears in the above-identified patent and that said Letters Patent is hereby corrected as shown below:

In column 1, line 17, after "Government Funding", insert the following:

--This invention was made with Government support under Grant No. DAAL03-90-G-0128 awarded by the Department of the Army and NIH-5R01-GM34077, awarded by the National Institutes of Health.--

In Claim 1, line 3, delete "compositions" and insert --composition--;

In Claim 1, line 4, delete "components" and insert --component--;

In Claim 19, line 3, delete "epidermis" and insert --stratum corneum-- for both the first and last words on the line;

In Claim 43, line 3, delete "epidermis" and insert --stratum corneum--;

In Claim 46, line 4, delete "epidermis" and insert --stratum corneum--;

UNITED STATES PATENT AND TRADEMARK OFFICE
CERTIFICATE OF CORRECTION

PATENT NO. : 5,749,847
DATED : May 12, 1998
INVENTOR(S) : Thomas E. Zewert, Uwe Pliquett, Robert S. Langer and James C. Weaver It is certified that error appears in the above-identified patent and that said Letters Patent is hereby corrected as shown below:

In Claim 48, lines 3-4, delete "epidermis" and insert --stratum corneum--; and

In Claim 49, lines 3-4, delete "epidermis" and insert --stratum corneum--.

Signed and Sealed this

Eighteenth Day of August, 1998

Attest:

BRUCE LEHMAN

Attesting Officer

Commissioner of Patents and Trademarks